United States Patent
Rezach

(10) Patent No.: US 8,470,009 B1
(45) Date of Patent: Jun. 25, 2013

(54) BONE FASTENER AND METHOD OF USE

(75) Inventor: William Alan Rezach, Atoka, TN (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 0 days.

(21) Appl. No.: 13/415,541

(22) Filed: Mar. 8, 2012

(51) Int. Cl.
*A61B 17/04* (2006.01)
*A61B 17/84* (2006.01)
*A61F 2/08* (2006.01)

(52) U.S. Cl.
USPC .......................... 606/300; 606/301; 606/305

(58) Field of Classification Search
USPC .............................. 606/246–278, 300–321
See application file for complete search history.

(56) References Cited

U.S. PATENT DOCUMENTS 8,048,125 B2 * 11/2011 Mitchell et al. ............... 606/264

\* cited by examiner

*Primary Examiner* — Eduardo C Robert
*Assistant Examiner* — Christina Negrellirodriguez

(57) ABSTRACT

A bone fastener comprises a proximal portion including an inner surface that defines a cavity. A carrier is disposed in fixed engagement with the inner surface. A pivoting member is disposed with the carrier and relatively moveable therefrom. A distal portion defines a longitudinal axis and is configured to penetrate tissue. The proximal portion is rotatable relative to the distal portion in a first plane of a body and the pivoting member is rotatable relative to the proximal portion in a second plane of the body. Methods of use are disclosed.

20 Claims, 9 Drawing Sheets

BONE FASTENER AND METHOD OF USE

TECHNICAL FIELD

The present disclosure generally relates to medical devices for the treatment of spinal disorders, and more particularly to a spinal implant system including a bone fastener that provides stabilization while reducing stress on spinal elements.

BACKGROUND

Spinal disorders such as degenerative disc disease, disc herniation, osteoporosis, spondylolisthesis, stenosis, scoliosis and other curvature abnormalities, kyphosis, tumor, and fracture may result from factors including trauma, disease and degenerative conditions caused by injury and aging. Spinal disorders typically result in symptoms including pain, nerve damage, and partial or complete loss of mobility.

Non-surgical treatments, such as medication, rehabilitation and exercise can be effective, however, may fail to relieve the symptoms associated with these disorders. Surgical treatment of these spinal disorders includes discectomy, laminectomy, fusion and implantable prosthetics. During surgical treatment, one or more rods may be attached via fasteners to the exterior of two or more vertebral members to provide stability to a treated region. This disclosure describes an improvement over these prior art technologies.

SUMMARY

Accordingly, a spinal implant system is provided. In one embodiment, in accordance with the principles of the present disclosure, the spinal implant system includes a bone fastener. The bone fastener comprises a proximal portion including an inner surface that defines a cavity. A carrier is disposed in fixed engagement with the inner surface. A pivoting member is disposed with the carrier and relatively moveable therefrom. A distal portion defines a longitudinal axis and is configured to penetrate tissue. The proximal portion is rotatable relative to the distal portion in a first plane of a body and the pivoting member is rotatable relative to the proximal portion in a second plane of the body.

In one embodiment, the spinal implant system includes at least one bone fastener comprising a receiver defining a first longitudinal axis and including spaced apart arms that include an inner surface of the receiver. At least a portion of the inner surface is threaded and engageable with a setscrew. The receiver further includes an extension. A carrier extends between a first end and a second end and includes a first surface disposed in fixed engagement with the inner surface and a second concave surface defining a first lateral opening and a second lateral opening. A saddle defines a first surface configured for slidable engagement with the second surface of the carrier along an arcuate path and a second concave surface that defines an implant cavity with the receiver defining a second axis transverse to the first longitudinal axis configured for disposal of an implant. The saddle includes a first arm that extends through the first lateral opening and a second arm that extends through the second lateral opening. The arms are engageable with the saddle to limit movement of the saddle. A tissue penetrating shaft extends between a first end and a second end. The first end includes a transverse channel configured for disposal of the extension. The spinal implant system also includes a vertebral rod. The bone fastener is movable between a first configuration such that the receiver is selectively rotatable relative to the shaft in a transverse plane of a body and the saddle is selectively rotatable relative to the receiver in a sagittal plane of the body, and a second configuration such that the setscrew applies a force to the rod disposed in the implant cavity and the rod engages the concave surface of the saddle to fix the bone fastener in an orientation.

In one embodiment, a method for treating a spine disorder is provided. The method comprises the steps of providing a bone fastener comprising: a proximal portion including an inner surface that defines a cavity, a carrier disposed in fixed engagement with the inner surface, a pivoting member disposed with the carrier and relatively moveable therefrom defining an implant cavity with the proximal portion, and a distal portion defining a longitudinal axis and being configured to penetrate tissue; attaching the distal portion with vertebrae; providing a vertebral rod disposed in an orientation; and selectively rotating the proximal portion relative to the distal portion in a first plane of a body, and selectively rotating the pivoting member relative to the proximal portion in a second plane of the body, to the orientation to dispose the rod in the implant cavity.

BRIEF DESCRIPTION OF THE DRAWINGS

The present disclosure will become more readily apparent from the specific description accompanied by the following drawings, in which.

Like reference numerals indicate similar parts throughout the figures.

DETAILED DESCRIPTION

Figure 1:
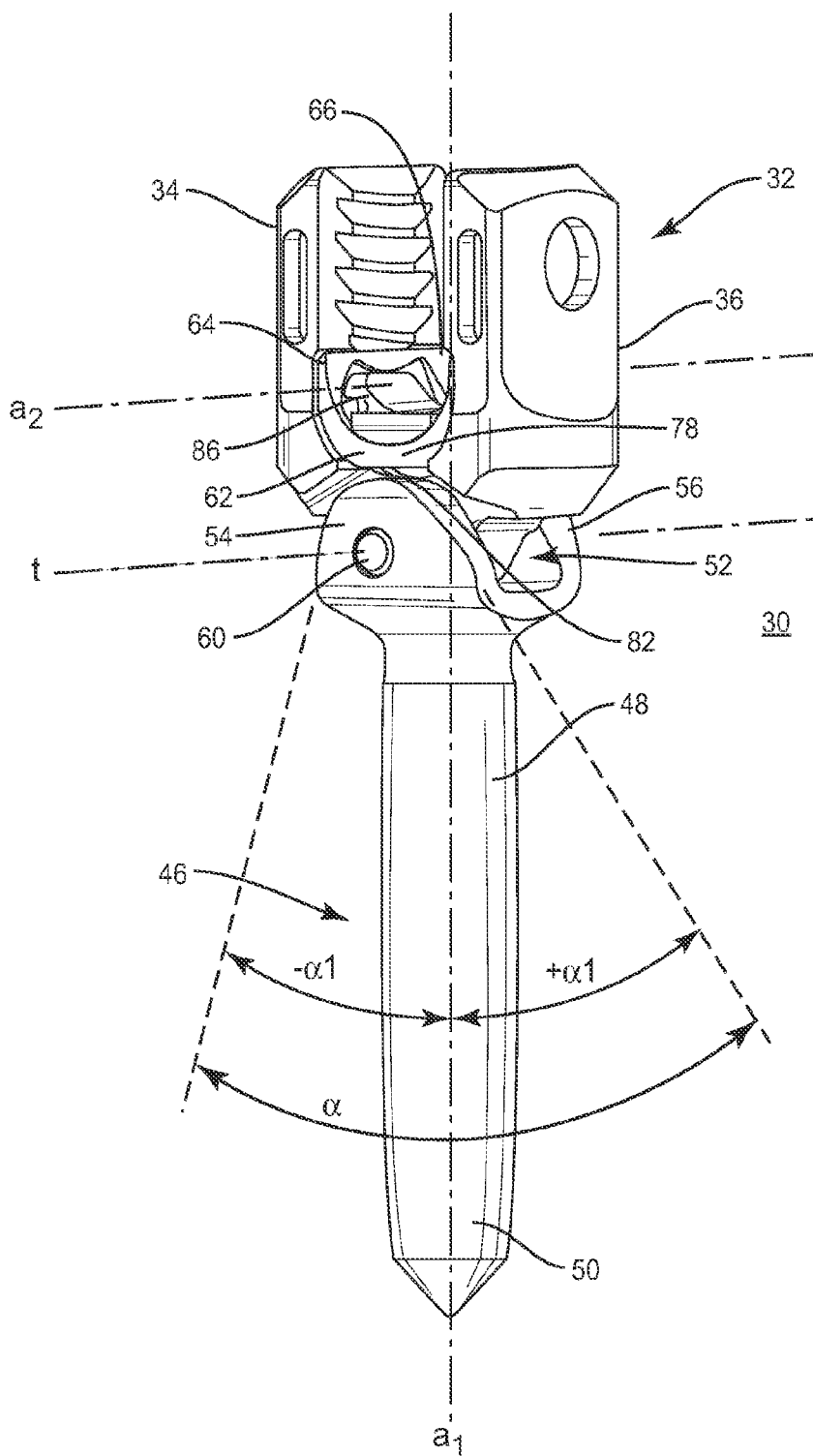
FIG. 1 is a perspective view of one embodiment of a bone fastener of a system in accordance with the principles of the present disclosure.
Figure 2:
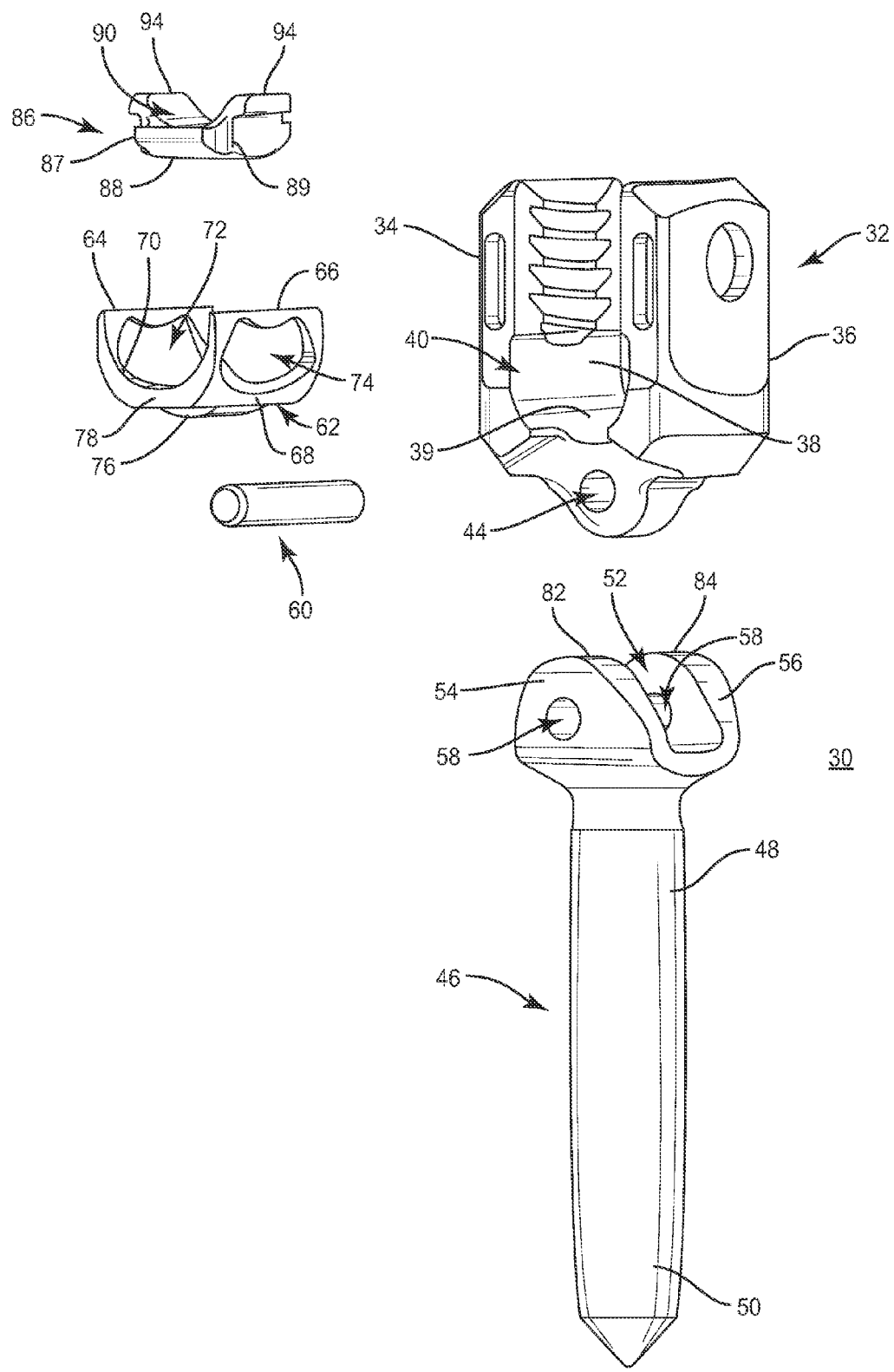
FIG. 2 is a perspective view of the bone fastener shown in FIG. 1 with parts separated.
Figure 3:
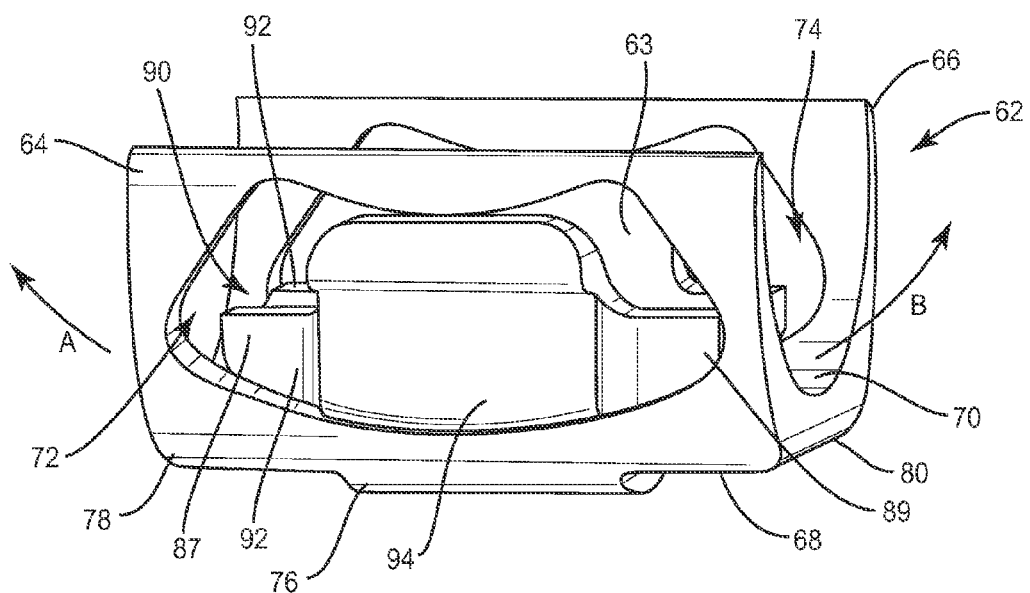
FIG. 3 is a perspective view of components of the bone fastener shown in FIG. 1.
Figure 4:
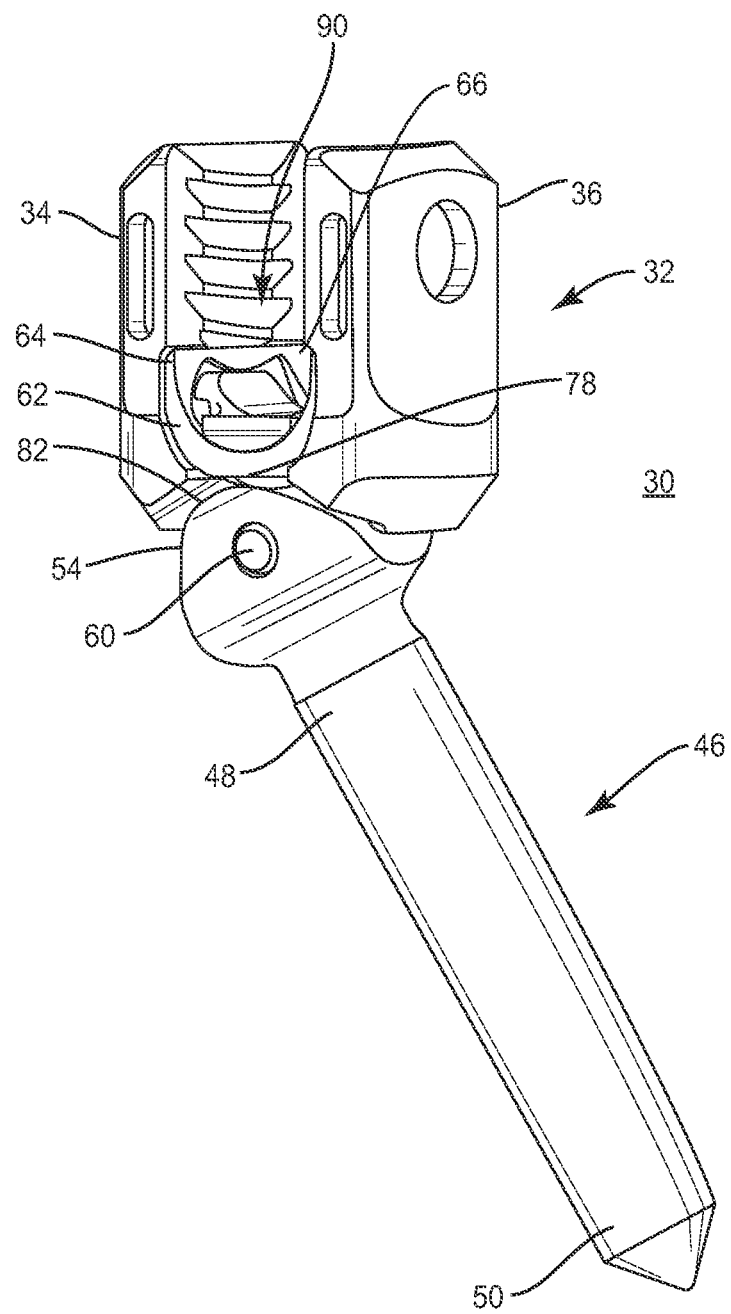
FIG. 4 is a perspective view of the bone fastener shown in FIG. 1.

The exemplary embodiments of a surgical system and methods of use disclosed are discussed in terms of medical devices for the treatment of spinal disorders and more particularly, in terms of a spinal implant system including a bone fastener that provides stabilization while reducing stress on spinal elements.

In one embodiment, the spinal implant system includes a transverse sagittal angulating and accommodating screw. The screw provides direct control of an implant. In one embodiment, this configuration allows sagittal accommodation to a spinal rod. It is envisioned that this configuration allows for sagittal manipulation once a spinal rod has been placed into the screw. It is further envisioned that the screw allows a head of the screw to pivot in a transverse plane of a body of a patient. It is contemplated that the screw may have a pivoting head combined with a pivoting saddle to allow sagittal accommodation to a spinal rod and sagittal manipulation once a spinal rod has been positioned within the head of the screw.

In one embodiment, the bone fastener provides independent transverse and sagittal movement that allows a surgeon to achieve more control during correction, which provides more precise correction. In one embodiment, the bone fastener includes a saddle that pivots approximately in a range of 26° in a sagittal plane. It is contemplated that such range can be measured +/−13° from an axis. In one embodiment, the bone fastener includes a head that pivots approximately in a range of 60° in a transverse plane. It is contemplated that such range can be measured +/−30° from an axis.

It is envisioned that the present disclosure may be employed to treat spinal disorders such as, for example, degenerative disc disease, disc herniation, osteoporosis, spondylolisthesis, stenosis, scoliosis and other curvature abnormalities, kyphosis, tumor and fractures. It is contemplated that the present disclosure may be employed with other osteal and bone related applications, including those associated with diagnostics and therapeutics. It is further contemplated that the disclosed surgical system and methods may be alternatively employed in a surgical treatment with a patient in a prone or supine position, and/or employ various surgical approaches to the spine, including anterior, posterior, posterior mid-line, lateral, postero-lateral, and/or antero-lateral approaches, and in other body regions. The present disclosure may also be alternatively employed with procedures for treating the lumbar, cervical, thoracic and pelvic regions of a spinal column. The system and methods of the present disclosure may also be used on animals, bone models and other non-living substrates, such as, for example, in training, testing and demonstration.

The present disclosure may be understood more readily by reference to the following detailed description of the disclosure taken in connection with the accompanying drawing figures, which form a part of this disclosure. It is to be understood that this disclosure is not limited to the specific devices, methods, conditions or parameters described and/or shown herein, and that the terminology used herein is for the purpose of describing particular embodiments by way of example only and is not intended to be limiting of the claimed disclosure. Also, as used in the specification and including the appended claims, the singular forms "a," "an," and "the" include the plural, and reference to a particular numerical value includes at least that particular value, unless the context clearly dictates otherwise. Ranges may be expressed herein as from "about" or "approximately" one particular value and/or to "about" or "approximately" another particular value. When such a range is expressed, another embodiment includes from the one particular value and/or to the other particular value. Similarly, when values are expressed as approximations, by use of the antecedent "about," it will be understood that the particular value forms another embodiment. It is also understood that all spatial references, such as, for example, horizontal, vertical, top, upper, lower, bottom, left and right, are for illustrative purposes only and can be varied within the scope of the disclosure. For example, the references "upper" and "lower" are relative and used only in the context to the other, and are not necessarily "superior" and "inferior".

Further, as used in the specification and including the appended claims, "treating" or "treatment" of a disease or condition refers to performing a procedure that may include administering one or more drugs to a patient (human, normal or otherwise or other mammal), in an effort to alleviate signs or symptoms of the disease or condition. Alleviation can occur prior to signs or symptoms of the disease or condition appearing, as well as after their appearance. Thus, treating or treatment includes preventing or prevention of disease or undesirable condition (e.g., preventing the disease from occurring in a patient, who may be predisposed to the disease but has not yet been diagnosed as having it). In addition, treating or treatment does not require complete alleviation of signs or symptoms, does not require a cure, and specifically includes procedures that have only a marginal effect on the patient. Treatment can include inhibiting the disease, e.g., arresting its development, or relieving the disease, e.g., causing regression of the disease. For example, treatment can include reducing acute or chronic inflammation; alleviating pain and mitigating and inducing re-growth of new ligament, bone and other tissues; as an adjunct in surgery; and/or any repair procedure. Also, as used in the specification and including the appended claims, the term "tissue" includes soft tissue, ligaments, tendons, cartilage and/or bone unless specifically referred to otherwise.

The following discussion includes a description of a spinal implant system including a bone fastener, related components and exemplary methods of employing the bone fastener in accordance with the principles of the present disclosure. Alternate embodiments are also disclosed. Reference will now be made in detail to the exemplary embodiments of the present disclosure, which are illustrated in the accompanying figures. Turning now to FIGS. 1-7, there is illustrated components of a spinal implant system including a bone fastener 30 in accordance with the principles of the present disclosure.

The components of the spinal implant system can be fabricated from biologically acceptable materials suitable for medical applications, including metals, synthetic polymers, ceramics and bone material and/or their composites, depending on the particular application and/or preference of a medical practitioner. For example, the components of bone fastener 30, individually or collectively, can be fabricated from materials such as stainless steel alloys, commercially pure titanium, titanium alloys, Grade 5 titanium, super-elastic titanium alloys, cobalt-chrome alloys, stainless steel alloys, superelastic metallic alloys (e.g., Nitinol, super elasto-plastic metals, such as GUM METAL® manufactured by Toyota Material Incorporated of Japan), ceramics and composites thereof such as calcium phosphate (e.g., SKELITE™ manufactured by Biologix Inc.), thermoplastics such as polyaryletherketone (PAEK) including polyetheretherketone (PEEK), polyetherketoneketone (PEKK) and polyetherketone (PEK), carbon-PEEK composites, PEEK-$BaSO_4$ polymeric rubbers, polyethylene terephthalate (PET), fabric, silicone, polyurethane, silicone-polyurethane copolymers, polymeric rubbers, polyolefin rubbers, hydrogels, semi-rigid and rigid materials, elastomers, rubbers, thermoplastic elastomers, thermoset elastomers, elastomeric composites, rigid polymers including polyphenylene, polyamide, polyimide, polyetherimide, polyethylene, epoxy, bone material including autograft, allograft, xenograft or transgenic cortical and/or corticocancellous bone, and tissue growth or differentiation factors, partially resorbable materials, such as, for example, composites of metals and calcium-based ceramics, composites of PEEK and calcium based ceramics, composites of PEEK with resorbable polymers, totally resorbable materials, such as, for example, calcium based ceramics such as calcium phosphate, tri-calcium phosphate (TCP), hydroxyapatite (HA)-TCP, calcium sulfate, or other resorbable polymers such as polyaetide, polyglycolide, polytyrosine carbonate, polycaroplaetohe and their combinations. Various components of the spinal implant system may have material composites, including the above materials, to achieve various desired characteristics such as strength, rigidity, elasticity, compliance, biomechanical performance, durability and radiolucency or imaging preference. The components of the spinal implant system, individually or collectively, may also be fabricated from a heterogeneous material such as a combination of two or more of the above-described materials. The components of the spinal implant system may be monolithically formed, integrally connected or include fastening elements and/or instruments, as described herein.

Bone fastener 30 comprises a proximal portion, such as, for example, a receiver 32 defining a first longitudinal axis $a_1$ and including spaced apart arms 34, 36 extending parallel to first longitudinal axis $a_1$. Receiver 32 includes an inner surface 38. It is contemplated that arm 34 and/or arm 36 may be disposed at alternate orientations, relative to first longitudinal axis $a_1$, such as, for example, transverse, perpendicular and/or other angular orientations such as acute or obtuse, co-axial and/or may be offset or staggered. Arms 34, 36 each include an arcuate outer surface. It is envisioned that the outer surfaces of arms 34, 36 may include a recess or cavity configured to receive an insertion tool, compression instrument and/or instruments for inserting and tensioning bone fastener 30.

Figure 8:
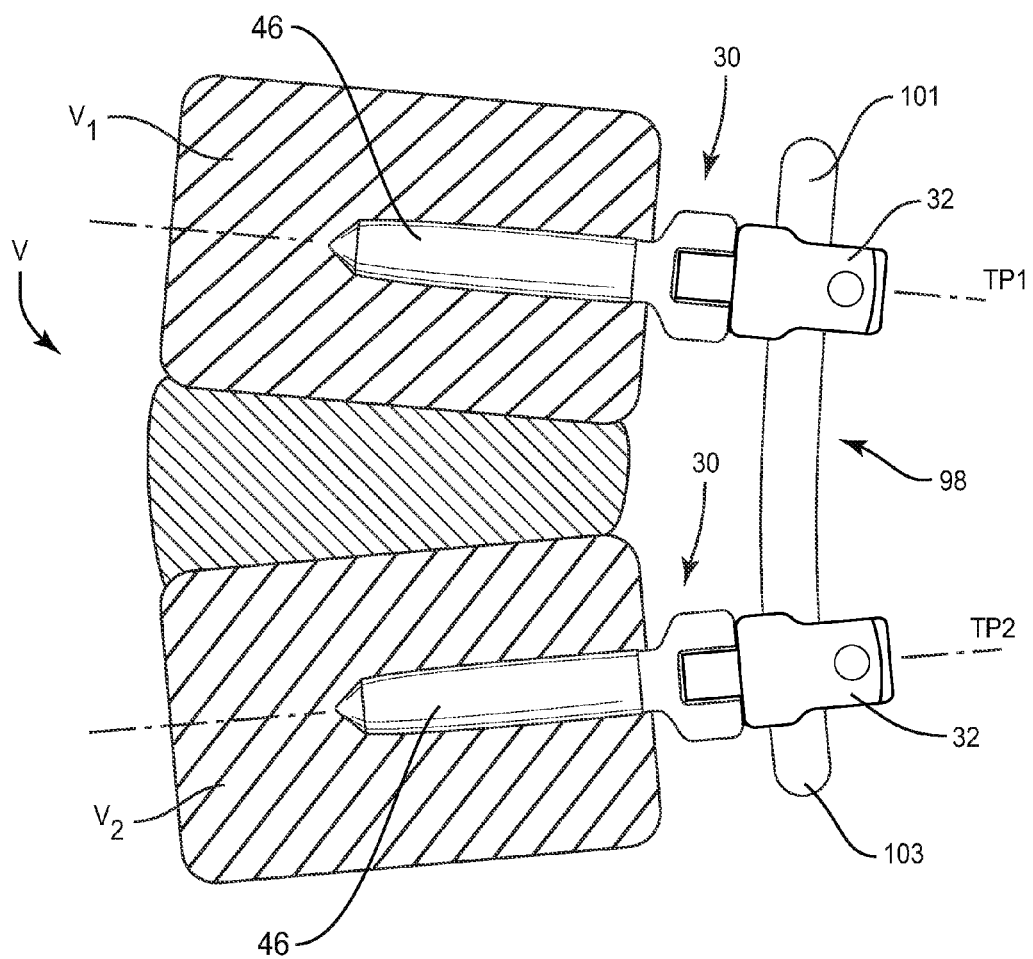
FIG. 8 is side view of a system in accordance with the principles of the present disclosure disposed with vertebrae.
Figure 9:
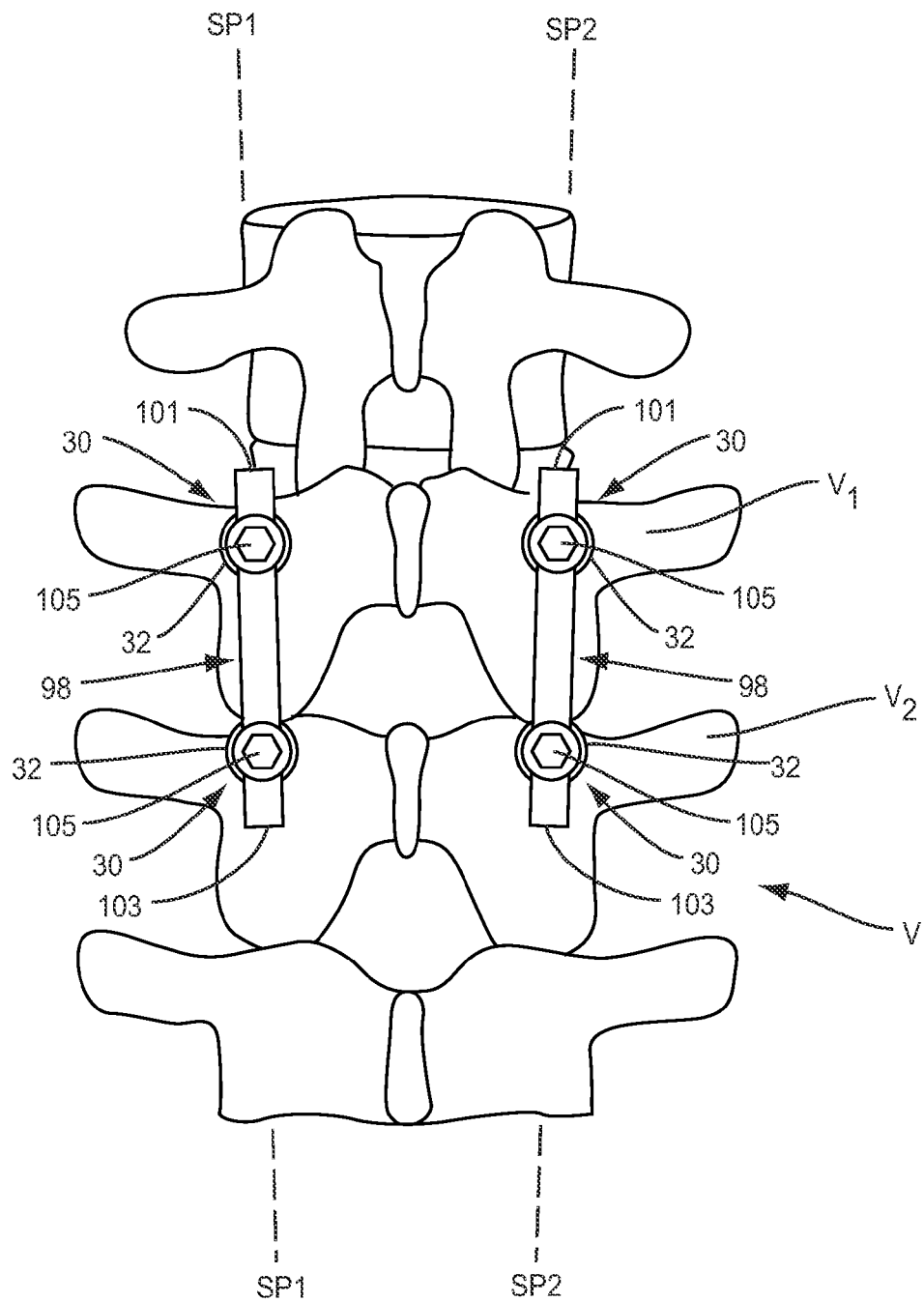
FIG. 9 is a plan view of the system shown in FIG. 8 disposed with vertebrae.

Inner surface 38 of receiver 32 defines a U-shaped cavity 40 extending between arms 34, 36. It is envisioned that all or only a portion of cavity 40 may have alternate cross section configurations, such as, for example, oval, oblong, triangular, square, polygonal, irregular, uniform, non-uniform, offset, staggered, and/or tapered. At least a portion of inner surface 38 is threaded and engageable with a setscrew (FIGS. 8 and 9). It is envisioned that inner surface 38 can include a thread form located adjacent arm 34 and a thread form located adjacent arm 36 each configured for engagement with a setscrew, as will be described. It is envisioned that inner surface 38 may be disposed with the setscrew in alternate fixation configurations, such as, for example, friction fit, pressure fit, locking protrusion/recess, locking keyway and/or adhesive. It is contemplated that all or only a portion of inner surface 38 may have alternate surface configurations to enhance fixation with the setscrew such as, for example, rough, arcuate, undulating, mesh, porous, semi-porous, dimpled and/or textured according to the requirements of a particular application.

Inner surface 38 of receiver 32 defines a concave surface 39 adjacent a base portion thereof and being configured to receive at least a portion of a carrier 62, described below, to retain the carrier with receiver 32. Concave surface 39 extends distally and is recessed from inner surface 38. It is envisioned that concave surface 39 may be disposed in the center of inner surface 38 such that concave surface 39 is equidistant from arm 34 and arm 36. It is further envisioned that concave surface 39 may also be offset such that concave surface 39 is disposed closer to arm 34 than arm 36, or vice versa. It is contemplated that concave surface 39 can extend into inner surface 38 without extending through a bottom surface of receiver 32. Concave surface 39 is configured to receive a corresponding convexly curved portion of carrier 62. It is contemplated that all or only a portion of concave surface 39 may be variously configured and dimensioned, such as, for example, oval, oblong, square, rectangular, polygonal, irregular, uniform, non-uniform, offset, staggered, tapered, consistent or variable, depending on the requirements of a particular application.

Receiver 32 includes an arcuate extension 42 extending distally from a distal end of receiver 32 between arms 34, 36. Extension 42 is configured for disposal in a longitudinal cavity in a distal portion of bone fastener 30, as will be described. It is envisioned that all or only a portion of extension 42 may be variously configured and dimensioned, such as, for example, planar, concave, polygonal, irregular, uniform, non-uniform, staggered, tapered, consistent or variable, depending on the requirements of a particular application.

Extension 42 includes an inner surface that defines a cavity, such as, for example, a first channel 44 extending therethrough along a transverse axis t of bone fastener 30 relative to first longitudinal axis $a_1$ so as to form a passageway configured to receive a transverse pin 60 to retain receiver 32 with a distal portion, such as, for example, shaft 46 of bone fastener 30. It is contemplated that first channel 44 may extend through extension 42 in various orientations relative to first longitudinal axis $a_1$, such as, for example, perpendicular and/or other angular orientations such as acute or obtuse and/or may be offset or staggered. First channel 44 has a tubular configuration for receiving cylindrical pin 60. It is envisioned that all or only a portion of first channel 44 may be variously configured and dimensioned, such as, for example, oval, oblong, square, rectangular, polygonal, irregular, uniform, non-uniform, offset, staggered, tapered, consistent or variable, depending on the requirements of a particular application.

Bone fastener 30 includes a tissue penetrating shaft 46 extending between a first end 48 and a second end 50 along first longitudinal axis $a_1$. Shaft 46 has a cylindrical cross section configuration that extends to a pointed distal tip. It is contemplated that shaft 46 may include an outer surface having an external threaded form. It is contemplated that the thread form on the outer surface of shaft 46 may include a single thread turn or a plurality of discrete threads. It is further contemplated that other engaging structures may be located on shaft 46, such as, for example, a nail configuration, barbs, expanding elements, raised elements and/or spikes to facilitate engagement of shaft 46 with tissue, such as, for example, vertebrae.

It is envisioned that all or only a portion of shaft 46 may have alternate cross section configurations, such as, for example, oval, oblong, triangular, square, polygonal, irregular, uniform, non-uniform, offset, staggered, undulating, arcuate, variable and/or tapered. It is contemplated that the outer surface of shaft 46 may include one or a plurality of openings. It is contemplated that all or only a portion of the outer surface of shaft 46 may have alternate surface configurations to enhance fixation with tissue such as, for example, rough, arcuate, undulating, mesh, porous, semi-porous, dimpled and/or textured according to the requirements of a particular application. It is envisioned that all or only a portion of shaft 46 may be disposed at alternate orientations, relative to first longitudinal axis $a_1$, such as, for example, transverse, perpendicular and/or other angular orientations such as acute or obtuse, co-axial and/or may be offset or staggered. It is further envisioned that all or only a portion of shaft 46 may be cannulated.

First end 48 of shaft 46 includes a cavity, such as, for example, a transverse channel 52 defined by a pair of convexly curved spaced apart arms 54, 56 extending proximally from first end 48. It is envisioned that at least a portion of arms 54, 56 may also be concavely curved or planar, according to the requirements of a particular application. Transverse channel 52 is substantially U-shaped and is configured for disposal of extension 42. The shape of transverse channel 52 is defined by planar inner surfaces of arms 54, 56 and a planar proximal face of first end 48, which is transverse to the planar inner surfaces of arms 54, 56 such that transverse channel 52 has a planar bottom wall and planar side walls extending transversely from either end of the planar bottom wall. It is envisioned that all or only a portion of transverse channel 52 may have alternate cross section configurations, such as, for example, oval, oblong, triangular, square, polygonal, irregular, uniform, non-uniform, offset, staggered, and/or tapered.

First end 48 of shaft 46 includes an inner surface that defines a second channel 58 extending through each of arms 54, 56 and transverse channel 52 transverse to first longitudinal axis $a_1$ so as to form a passageway configured to receive transverse pin 60 to retain receiver 32 with shaft 46. It is contemplated that second channel 58 may extend through arms 54, 56 in other orientations relative to first longitudinal axis $a_1$, such as, for example, perpendicular and/or other angular orientations such as acute or obtuse and/or may be offset or staggered. Second channel 58 has a tubular configuration for receiving pin 60. It is envisioned that all or only a portion of second channel 58 may be variously configured and dimensioned, such as, for example, oval, oblong, square, rectangular, polygonal, irregular, uniform, non-uniform, offset, staggered, tapered, consistent or variable, depending on the requirements of a particular application. Second channel 58 has a diameter that is approximately the same as a diameter of first channel 44 of extension 42. Transverse pin 60 has a diameter that is less than that of first and second channels 44, 58 such that pin 60 may be received within first and second channels 44, 58.

To engage receiver 32 with shaft 46, extension 42 of receiver 32 is inserted into transverse channel 52 such that channels 44, 58 are aligned. Transverse pin 60 is inserted through channels 44, 58 such that pin 60 engages at least a portion of receiver 32 and shaft 46 to connect receiver 32 with shaft 46. Receiver 32 is selectively rotatable relative to shaft 46 within a first plane, such as, for example, a transverse plane TP (FIG. 8) of a body of a patient.

Figure 6:
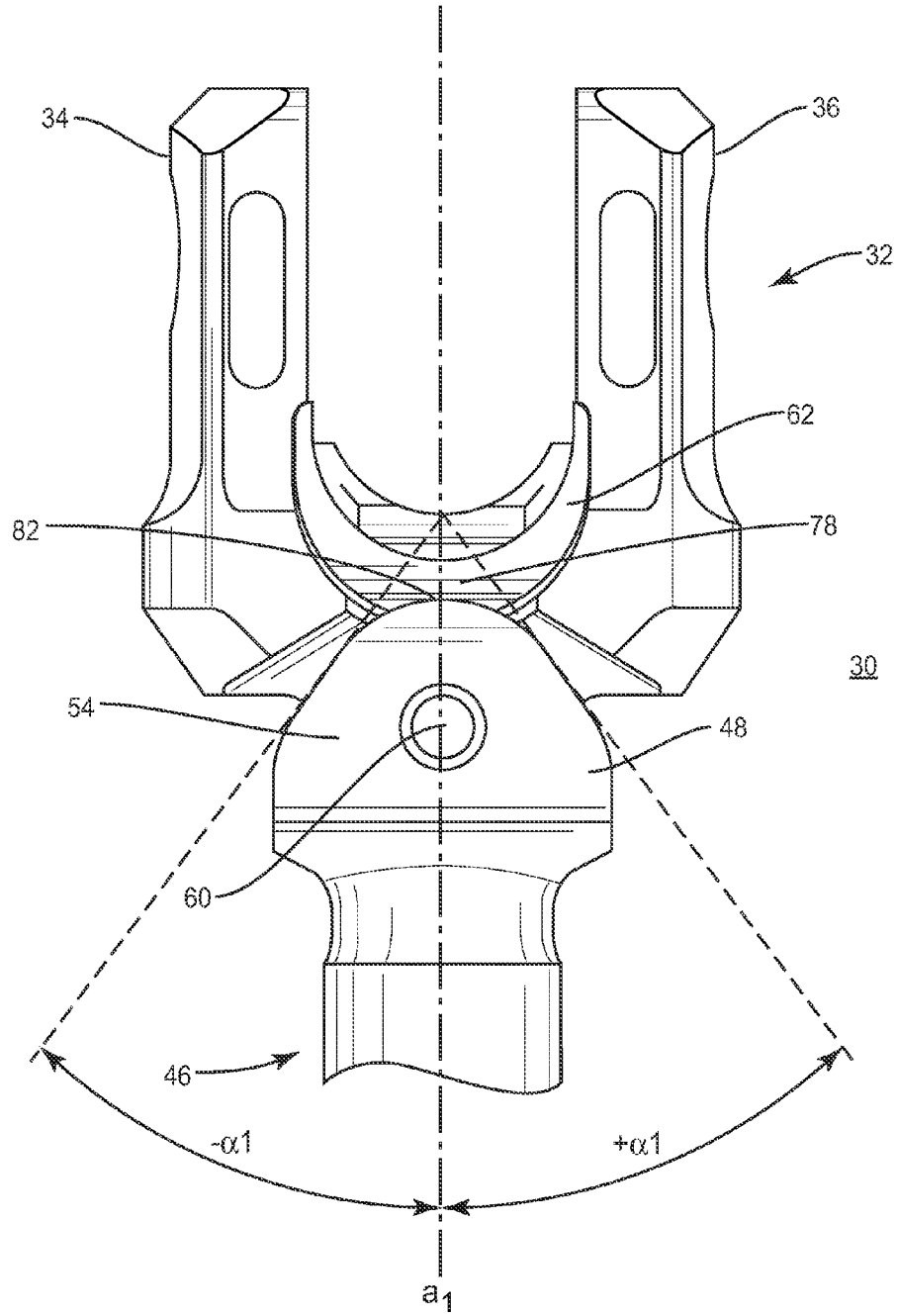
FIG. 6 is a break away side view of the bone fastener shown in FIG. 1.

Receiver 32 and shaft 46 are relatively rotatable about transverse axis t, for example, such that shaft 46 is rotatable relative to receiver 32 through an angular range α (FIGS. 1 and 6). Shaft 46 is pivotable through angular range α at +/− an angle α1 relative to axis $a_1$. It is contemplated that angular range α may include a range of approximately 0 to 60 degrees. It is further contemplated that angle α1 may include a range of approximately +/−30 degrees.

Figure 7:
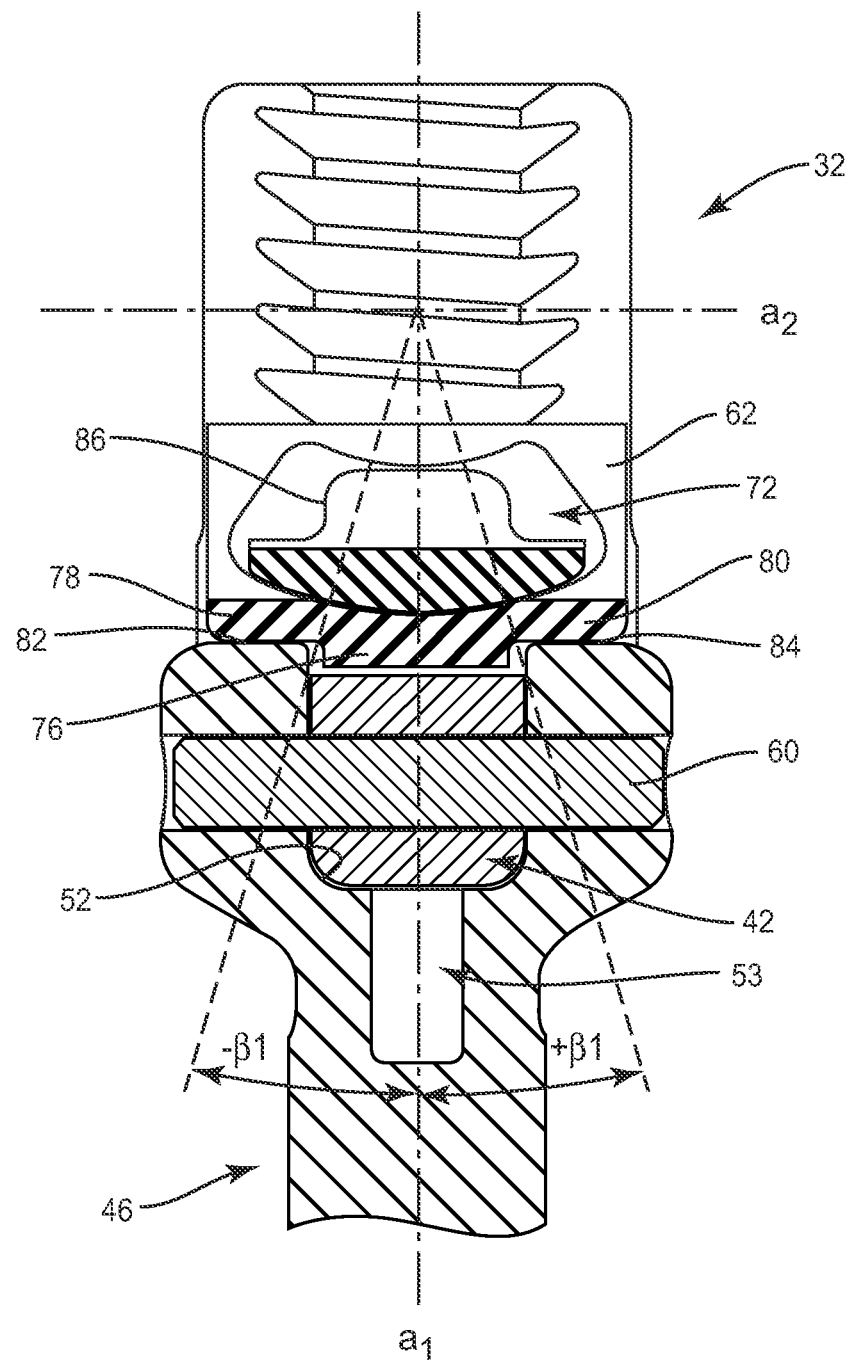
FIG. 7 is a break away side view, in cross section, of the bone fastener shown in FIG. 1.

Pin 60 is beveled at either end, as shown in FIG. 7, to facilitate insertion of pin 60 into channels 44, 58. It is contemplated that receiver 32 may be disposed with shaft 46 for relative movement in orientations relative to first longitudinal axis $a_1$, such as, for example, transverse, perpendicular and/or other angular orientations such as acute or obtuse, co-axial and/or may be offset or staggered. It is further contemplated that receiver 32 may move relative to shaft 46 in alternate planes relative to a body, such as, for example, vertical, horizontal, diagonal, transverse, coronal and/or sagittal planes of a body. It is envisioned that receiver 32 may be retained with shaft 46 in alternate fixation configurations, such as, for example, friction fit, pressure fit, locking protrusion/recess, locking keyway and/or adhesive.

Arms 54, 56 include convexly curved interference surfaces 82, 84 disposed along an exterior surface thereof configured to engage corresponding interference surfaces on carrier 62 to prevent receiver 32 from moving relative to shaft 46 upon fixation within an orientation of bone fastener 30, as will be described. It is envisioned that interference surfaces 82, 84 may also be concavely curved, irregular or planar, according to the requirements of a particular application. It is further envisioned that all or only a portion of interference surfaces 82, 84 may have alternate surface configurations to enhance fixation with carrier 62 such as, for example, rough, arcuate, undulating, mesh, porous, semi-porous, dimpled and/or textured according to the requirements of a particular application.

Carrier 62 is defined by opposing arms 64, 66. Carrier 62 includes a first surface 68 configured for fixed engagement with inner surface 38 of receiver 32 and a second concave surface 70. Surface 70 defines a first lateral opening 72 in arm 64 and a second lateral opening 74 in arm 66. First surface 68 includes a projection 76 extending distally therefrom along first longitudinal axis $a_1$ and being configured for receipt within concave surface 39. This configuration retains carrier 62 with receiver 32 and prevents movement of carrier 62 within cavity 40 of receiver 32. Projection 76 is centrally disposed with carrier 62. It is envisioned that projection 76 may also be offset. It is envisioned that receiver 32 may be retained with carrier 62 in alternate fixation configurations, such as, for example, friction fit, pressure fit, locking protrusion/recess, locking keyway and/or adhesive.

Figure 5:
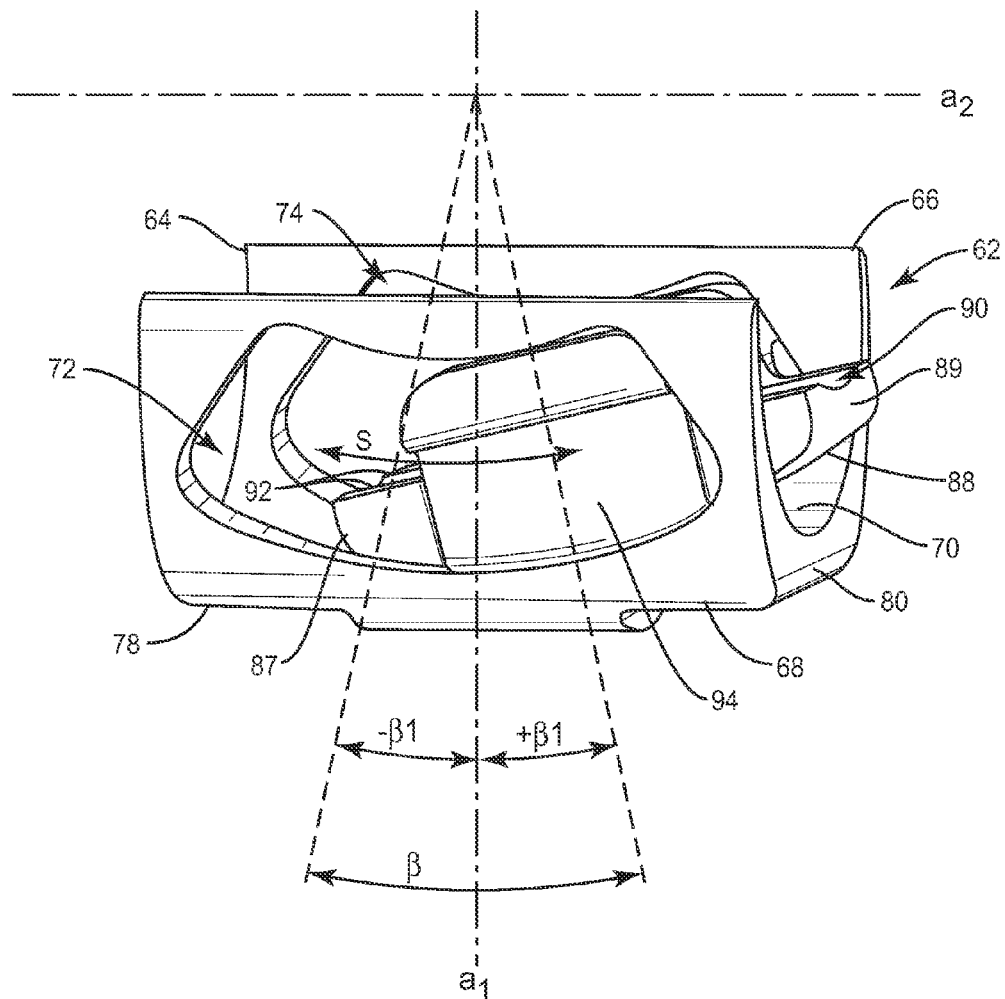
FIG. 5 is a perspective view of components of the bone fastener shown in FIG. 1.

Second surface 70 of carrier 62 is configured for disposal of a pivoting member 86, described below. First and second lateral openings 72, 74 each include concavely curved top and bottom surfaces extending between planar side surfaces so as to define an arcuate path S, as shown in FIG. 5. The side surfaces of first and second lateral openings 72, 74 are disposed at an angle of approximately 45 degrees relative to first longitudinal axis $a_1$. It is contemplated that the side surfaces of first and second lateral openings 72, 74 may be disposed at an angle of approximately 0 to 90 degrees relative to first longitudinal axis $a_1$ and/or may be offset or staggered, or may be disposed at alternate orientations relative to first longitudinal axis $a_1$, such as, for example, transverse, perpendicular and/or other angular orientations such as acute or obtuse, co-axial. First and second lateral openings 72, 74 are disposed in parallel relation. It is contemplated that lateral openings 72, 74 may be disposed at alternate orientations, such as, for example, transverse, and/or other angular orientations such as acute or obtuse, and/or may be offset or staggered.

First and second lateral openings 72, 74 are configured for movement of the pivoting member, such as, for example, a saddle 86. Saddle 86 is moveable relative to carrier 62 in a first direction, as shown by arrow A in FIG. 3 and a second direction opposite to the first direction, as shown by arrow B.

Saddle 86 extends between a first end 87 and a second end 89 and is disposed with carrier 62. Saddle 86 defines a first surface 88 configured for slidable engagement with second surface 70 of carrier 62 along arcuate path S. Saddle 86 defines a second concave surface 63 that defines an implant cavity 90 with receiver 32. Implant cavity 90 defines a second axis $a_2$ transverse to first longitudinal axis $a_1$ and parallel to transverse axis t. Implant cavity 90 is configured to receive and movably support at least a portion of an implant, such as, for example, a vertebral rod 98 (FIGS. 8 and 9). Rod 98 can translate axially relative to implant cavity 90 along second axis $a_2$ prior to fixation and is pivotable with saddle 86. It is contemplated that at least a portion of rod 98 may be disposed within implant cavity 90 for relative movement in orientations relative to second axis $a_2$, such as, for example, transverse, perpendicular and/or other angular orientations such as acute or obtuse, co-axial and/or may be offset or staggered. It is envisioned that implant cavity 90 may have alternate cross section configurations, such as, for example, oval, oblong, triangular, rectangular, square, polygonal, irregular, uniform, non-uniform, variable and/or tapered.

First surface 88 of saddle 86 is curved between first and second ends 87, 89 for slidable engagement with first and second lateral openings 72, 74 and second surface 70 of carrier 62. Saddle 86 includes a pair of opposite sidewalls 92 and tabs 94 that are configured to extend through lateral openings 72, 74. Saddle 86 translates relative to carrier 62 along arcuate path S as limited by the boundaries defined by lateral openings 72, 74 and their engagement with tabs 94.

It is envisioned that saddle 86 may be elastic and pliable in a configuration to react to forces applied and/or force changes, such as, for example, patient growth, trauma and degeneration, and/or component creep, deformation, damage and degeneration, to maintain the applied force transmitted from an implant positioned in implant cavity 90 substantially constant. It is contemplated that saddle 86 can facilitate maintenance of a holding force on an implant positioned in implant cavity 90 to remain the holding force relatively constant despite growth and changes to bone fastener 30.

Saddle 86 translates relative to carrier 62 along arcuate path S such that saddle 86 is selectively rotatable relative to receiver 32 in a second plane, such as, for example, a sagittal plane SP (FIG. 9) of a body of a patient. Saddle 86 is rotatable about second axis $a_2$ through an angular range $\beta$ (FIGS. 5 and 7). Saddle 86 is pivotable along arcuate path S in slidable engagement with carrier 62 through angular range $\beta$ at +/− an angle $\beta1$ relative to axis $\alpha1$. It is contemplated that angular range $\beta$ may include a range of approximately 0 to 26 degrees. It is further contemplated that angle $\beta1$ may include a range of approximately +/−13 degrees.

Carrier 62 includes an interference surface 78 and an interference surface 80 that extend beyond cavity 40 of receiver 32 when carrier 62 is retained with receiver 32. Interference surfaces 78, 80 overlap interference surfaces 82, 84 when carrier 62 is retained with receiver 32. Interference surfaces 78, 80 are substantially planar and are configured to engage interference surfaces 82, 84 of arms 54, 56 to prevent receiver 32 from moving relative to shaft 46 when bone fastener 30 is disposed in a fixed orientation. In one embodiment, a force from a setscrew is applied to a vertebral rod disposed in implant cavity 90 such that the vertebral rod transmits the force to carrier 62. This force transmission causes interference surfaces 78, 80 to engage interference surfaces 82, 84 to fix bone fastener 30 in an orientation.

In assembly, operation and use, a spinal implant system including bone fastener 30, similar to that described above, is employed with a surgical procedure for treatment of a spinal disorder affecting a section of a spine of a patient, as discussed herein. In particular, the spinal implant system is employed with a surgical procedure for treatment of a condition or injury of an affected section of the spine including vertebrae V, as shown in FIGS. 8 and 9. It is contemplated that the spinal implant system including bone fastener 30 is attached to vertebrae V for a surgical arthrodesis procedure, such as fusion, and/or dynamic stabilization application of the affected section of the spine to facilitate healing and therapeutic treatment.

In use, to treat the affected section of the spine, a medical practitioner obtains access to a surgical site including vertebra V in any appropriate manner, such as through incision and refraction of tissues. It is envisioned that the spinal implant system including bone fastener 30 may be used in any existing surgical method or technique including open surgery, mini-open surgery, minimally invasive surgery and percutaneous surgical implantation, whereby the vertebrae V is accessed through a micro-incision, or sleeve that provides a protected passageway to the area. Once access to the surgical site is obtained, the particular surgical procedure is performed for treating the spinal disorder. Bone fastener 30 is then employed to augment the surgical treatment. The spinal implant system including bone fastener 30 and vertebral rod 98 can be delivered or implanted as a pre-assembled device or can be assembled in situ. The spinal implant system may be completely or partially revised, removed or replaced.

Pilot holes are made in vertebrae $V_1$ and $V_2$ for receiving shafts 46 of bone fasteners 30. Shafts 46 of first and second bone fasteners 30 are inserted or otherwise connected to vertebrae $V_1$ and $V_2$ according to the particular requirements of the surgical treatment. A pair of bone fasteners 30 are configured to attach upper sections 101 of rods 98 to vertebra $V_1$ and a pair of bone fasteners 30 are configured to attach lower sections 103 of rods 98 to adjacent vertebra $V_2$.

With shafts 46 connected to vertebrae $V_1$ and $V_2$, bone fasteners 30 are moveable between a first configuration and a second configuration. In the first configuration, each receiver 32 is attached with a shaft 46 such that receiver 32 is selectively and freely rotatable relative to shaft 46 within transverse planes TP1 and TP2 (FIG. 8), respectively, of vertebrae V. Saddle 86 is selectively and freely translatable along arcuate path S relative to receiver 32 in sagittal planes SP1 and SP2 (FIG. 9), respectively, of vertebrae V.

According to the orientation and position of sections 101, 103 of each rod 98, bone fasteners 30 are independently and selectively moved to a second configuration such that each implant cavity 90 of receiver 32 is selectively rotatable relative to shaft 46 within transverse planes TP1 and TP2. Implant cavity 90 is relatively rotatable about transverse axis t such that receiver 32 rotates through an angular range a (FIGS. 1 and 6) relative to axis $a_1$. This configuration allows orientation of implant cavity 90 to receive each of sections 101, 103 such that receivers 32 can capture rods 98.

Saddle 86 translates relative to carrier 62 along path S and is rotatable about second axis $a_2$ through an angular range $\beta$ in sagittal planes SP1 and SP2 to receive, engage and accommodate the orientation and position of sections 101, 103. Sections 101, 103 may also engage the individual saddles 86 to cause translation of a saddle 86 along path S.

In the second configuration, set screws 105 are torqued and threaded with each receiver 32 to securely attach rods 98 with vertebrae $V_1$, $V_2$. Each setscrew 105 is threaded into the threaded portion of inner surface 38 of receiver 32 such that setscrew 105 engages rod 98. As setscrew 105 is threaded into receiver 32, setscrew 105 applies a force to rod 98 disposed implant cavity 90. This force is transmitted through rod 98 such that rod 98 engages saddle 86. The force is transmitted through saddle 86 to carrier 62 causing interference surfaces 78, 80 to engage interference surfaces 82, 84, as described above. This configuration fixes bone fastener 30 in an orientation of shaft 46 with receiver 32 to prevent receiver 32 from moving relative to shaft 46 and to fix bone fastener 30 in an orientation to receive and accommodate the orientation and position of sections 101, 103.

In one embodiment, as shown in FIG. 7, first end 48 of shaft 46 includes a longitudinal cavity 53 extending distally from and in communication with transverse channel 52 along first longitudinal axis $a_1$. Longitudinal cavity 53 is configured for disposal of a biasing member, such as, for example, a silicone member or a spring that applies a resilient force to receiver 32 to maintain a force applied to bone fastener 30.

Bone fastener 30 may be employed as a bone screw, pedicle screw or multi-axial screw used in spinal surgery. In one embodiment, the spinal implant system includes an agent, which may be disposed, packed or layered within, on or about the surfaces of bone fastener 30. It is envisioned that the agent may include bone growth promoting material, such as, for example, bone graft to enhance fixation of the fixation elements with vertebrae.

It is contemplated that the agent may include therapeutic polynucleotides or polypeptides. It is further contemplated that the agent may include biocompatible materials, such as, for example, biocompatible metals and/or rigid polymers, such as, titanium elements, metal powders of titanium or titanium compositions, sterile bone materials, such as allograft or xenograft materials, synthetic bone materials such as coral and calcium compositions, such as HA, calcium phosphate and calcium sulfite, biologically active agents, for example, gradual release compositions such as by blending in a bioresorbable polymer that releases the biologically active agent or agents in an appropriate time dependent fashion as the polymer degrades within the patient. Suitable biologically active agents include, for example, BMP, Growth and Differentiation Factors proteins (GDF) and cytokines. The components of the spinal implant system can be made of radiolucent materials such as polymers. Radiomarkers may be included for identification under x-ray, fluoroscopy, CT or other imaging techniques. It is envisioned that the agent may include one or a plurality of therapeutic agents and/or pharmacological agents for release, including sustained release, to treat, for example, pain, inflammation and degeneration.

It is envisioned that the use of microsurgical and image guided technologies may be employed to access, view and repair spinal deterioration or damage, with the aid of the spinal implant system. Upon completion of a procedure employing the spinal implant system described above, the surgical instruments and assemblies are removed and the incision is closed.

It will be understood that various modifications may be made to the embodiments disclosed herein. Therefore, the above description should not be construed as limiting, but merely as exemplification of the various embodiments. Those skilled in the art will envision other modifications within the scope and spirit of the claims appended hereto.

What is claimed is:

1. A bone fastener comprising:
   a proximal portion including an inner surface that defines a cavity;
   a carrier disposed in fixed engagement with the inner surface;
   a pivoting member being disposed within a concave surface of the carrier and relatively moveable therefrom, the concave surface defining at least one lateral opening configured for movement of the pivoting member therein; and
   a distal portion defining a longitudinal axis and being configured to penetrate tissue;
   wherein the proximal portion is rotatable relative to the distal portion in a first plane of a body and the pivoting member is rotatable relative to the proximal portion in a second plane of the body.

2. A bone fastener as recited in claim 1, wherein the carrier includes a first surface configured for fixation with the inner surface.

3. A bone fastener as recited in claim 1, wherein the pivoting member is movable relative to the carrier in a first direction and a second direction opposite to the first direction.

4. A bone fastener as recited in claim 1, wherein the carrier extends beyond the proximal portion to overlap the distal portion.

5. A bone fastener as recited in claim 1, wherein the carrier includes an interference surface that extends beyond the proximal portion to engage an interference surface of the distal portion.

6. A bone fastener as recited in claim 1, wherein the distal portion defines a cavity configured for disposal of the proximal portion.

7. A bone fastener as recited in claim 1, wherein the distal portion defines a cavity configured for disposal of the proximal portion, the cavity being configured for disposal of a biasing member that engages the proximal portion.

8. A bone fastener as recited in claim 1, further comprising a transverse pin, wherein the distal portion defines a cavity configured for disposal of the proximal portion and the pin extends through the proximal portion and the distal portion to retain the proximal portion with the distal portion.

9. A bone fastener as recited in claim 1, wherein the pivoting member is configured for translation relative to the carrier along an arcuate path.

10. A bone fastener as recited in claim 1, wherein the pivoting member defines a first surface configured for slidable engagement with the carrier and a second concave surface configured for engagement with an implant.

11. A bone fastener as recited in claim 1, wherein the pivoting member defines an implant cavity with the proximal portion.

12. A bone fastener as recited in claim 1, wherein the first plane is a transverse plane of the body and the second plane is a sagittal plane of the body.

13. A bone fastener as recited in claim 1, wherein the proximal portion is rotatable in a range of approximately 0 to 60 degrees relative to the distal portion.

14. A bone fastener as recited in claim 1, wherein the pivoting member is rotatable in a range of approximately 0 to 30 degrees relative to the proximal portion.

15. A bone fastener as recited in claim 1, wherein the proximal portion is selectively rotatable to an angular orientation in a range of approximately 0 to 60 degrees relative to the distal portion within the first plane.

16. A bone fastener as recited in claim 1, wherein the pivoting member is selectively rotatable to an angular orientation in a range of approximately 0 to 30 degrees relative to the proximal portion within the second plane.

17. A bone fastener as recited in claim 1, wherein the at least one lateral opening includes first and second lateral openings each including concavely curved top and bottom surfaces extending between planar side surfaces such that the first and second lateral openings define an arcuate path.

18. A spinal implant system comprising:
    at least one bone fastener comprising:
        a receiver defining a first longitudinal axis and including spaced apart arms that include an inner surface of the receiver, at least a portion of the inner surface being threaded and engageable with a setscrew, the receiver further including an extension,
        a carrier extending between a first end and a second end, the carrier including a first surface disposed in fixed engagement with the inner surface and a second concave surface defining a first lateral opening and a second lateral opening,
        a saddle defining a first surface configured for slidable engagement with the second surface of the carrier along an arcuate path and a second concave surface that defines an implant cavity with the receiver, the implant cavity defining a second axis transverse to the first longitudinal axis and being configured for disposal of an implant, the saddle including a first arm that extends through the first lateral opening and a second arm that extends through the second lateral opening, the arms being engageable with the saddle to limit movement of the saddle, and
        a tissue penetrating shaft extending between a first end and a second end, the first end including a cavity configured for disposal of the extension; and a vertebral rod, wherein the bone fastener is movable between a first configuration such that the receiver is selectively rotatable relative to the shaft in a transverse plane of a body and the saddle is selectively rotatable relative to the receiver in a sagittal plane of the body, and a second configuration such that the setscrew applies a force to the rod disposed in the implant cavity and the rod engages the concave surface of the saddle to fix the bone fastener in an orientation.

19. A method for treating a spine disorder, the method comprising the steps of:

providing a bone fastener comprising:

a proximal portion including an inner surface that defines a cavity, a carrier disposed in fixed engagement with the inner surface, a pivoting member being disposed with the carrier and relatively moveable therefrom, the pivoting member defining an implant cavity with the proximal portion, and a distal portion defining a longitudinal axis and being configured to penetrate tissue;

attaching the distal portion with vertebrae;

providing a vertebral rod disposed in an orientation; and selectively rotating the proximal portion relative to the distal portion in a first plane of a body, and selectively rotating the pivoting member relative to the proximal portion in a second plane of the body, to the orientation to dispose the rod in the implant cavity.

20. A method as recited in claim 19, further comprising the step of applying a force to the rod disposed in the implant cavity such that the rod engages the pivoting member to fix the bone fastener in the orientation.

* * * * *